(12) United States Patent
Fahl

(10) Patent No.: US 10,390,942 B2
(45) Date of Patent: Aug. 27, 2019

(54) SPEECH VALVE FOR PERSONS HAVING UNDERGONE A LARYNGECTOMY OR TRACHEOTOMY

(71) Applicant: Andreas Fahl Medizintechnik—Vertrieb GmbH, Cologne (DE)

(72) Inventor: Andreas Fahl, Köln (DE)

(73) Assignee: ANDREAS FAHL MEDIZINTECHNIK—VERTRIEB GMBH, Cologne (DE)

( * ) Notice: Subject to any disclaimer, the term of this patent is extended or adjusted under 35 U.S.C. 154(b) by 520 days.

(21) Appl. No.: 15/145,310

(22) Filed: May 3, 2016

(65) Prior Publication Data

US 2016/0242900 A1    Aug. 25, 2016

Related U.S. Application Data

(63) Continuation of application No. PCT/EP2014/002934, filed on Nov. 3, 2014.

(30) Foreign Application Priority Data

Nov. 4, 2013   (DE) .................. 10 2013 018 423

(51) Int. Cl.
```
A61F 2/20       (2006.01)
A61M 16/04      (2006.01)
A61M 16/10      (2006.01)
```
(52) U.S. Cl.
CPC .......... *A61F 2/20* (2013.01); *A61M 16/0468* (2013.01); *A61M 16/1045* (2013.01); *A61F 2002/206* (2013.01); *A61M 16/047* (2013.01)

(58) Field of Classification Search
CPC ................................. A61F 2/20; A61M 16/00

USPC ............................................................ 623/9
See application file for complete search history.

(56) References Cited

U.S. PATENT DOCUMENTS 5,738,095 A    4/1998   Persson

FOREIGN PATENT DOCUMENTS

| DE | 69920440 | 10/2005 |
|---|---|---|
| DE | 202012001825 U1 | 4/2012 |
| DE | 202013001950 | 3/2013 |
| DE | 202013008092 | 10/2013 |
| EP | 2236165 | 10/2010 |

(Continued)

OTHER PUBLICATIONS

International Search Report dated Jan. 20, 2015, International Patent Application No. PCT/EP2014/002934 filed Nov. 3, 2014.

*Primary Examiner* — Yashita Sharma
(74) *Attorney, Agent, or Firm* — Dinsmore & Shohl LLP

(57) ABSTRACT

To solve the problem of making available a speech valve for persons who have undergone a laryngectomy or tracheotomy, which speech valve in particular has a long useful life, a speech valve (10) is proposed having a housing (12) with a proximal opening (14) and at least one filter (70) at least partially received in the housing, and with a piston-like valve element (30), wherein the filter at least partially surrounds the valve element, wherein the valve element is movable on a valve seat (32), arranged on the proximal opening, in order to produce a closure position and can be returned with a spring action to an open position of the speech valve, and wherein the valve element has a lower end (38) which faces towards the proximal opening and which is assigned to the valve seat in the open position and, with the valve seat, forms a gap (40) through which an air stream (17a) can be guided.

9 Claims, 3 Drawing Sheets

(56) References Cited

FOREIGN PATENT DOCUMENTS

| | | |
|---|---|---|
| WO | 2011144237 | 11/2011 |
| WO | 2012048681 | 4/2012 |

SPEECH VALVE FOR PERSONS HAVING UNDERGONE A LARYNGECTOMY OR TRACHEOTOMY

CROSS-REFERENCE TO RELATED APPLICATIONS

This application is a continuation of PCT Patent Application PCT/EP2014/002934 filed on Nov. 3, 2014, which claims priority of German Patent Application 10 2013 018 423.1 filed on Nov. 4, 2013.

FIELD OF THE INVENTION

The present invention relates to a speech valve for persons having undergone a laryngectomy or tracheotomy, having at least one housing with a proximal opening, i.e. close to the body, and at least one filter received at least partially in the housing.

BACKGROUND OF THE INVENTION

Speech valves of the type specified above are known in a variety of forms, and connect two substantial properties in a single device, specifically, on one hand, they provide moisture in the air that is breathed, and on the other hand, they enable a person having undergone a laryngectomy or tracheotomy to speak, in transitioning from an open position into a closure position.

With surgical interventions in the upper respiratory tract, the insertion of an artificial breathing hole (tracheostoma) in the trachea may be necessary, in order that air may be inhaled directly into the lungs, bypassing the oral cavity and larynx. With persons having undergone a laryngectomy or tracheotomy, filter systems are normally used, which are composed of an adhesive bandage having a filter inserted therein, normally made of a self-adhesive base plate, or a tracheal cannula—normally made of plastic—in which filters of different types can be inserted. The filter systems, which are used in laryngotracheal items, such as tracheal cannulas and bandages or base plates, include the so-called moisture and heat exchangers, also called artificial noses. These serve to reproduce missing regulation mechanisms for heating and moistening the breathing air for persons having undergone a tracheotomy, or a laryngectomy, and to prevent the trachea from coming in contact with dry, cold and unfiltered air. This is because mucous production increases with the irritation caused thereby, accompanied by the danger of clogging as a consequence. The inhaled air is moistened, heated and simultaneously filtered by the moisture and heat exchanger. As a result, the aforementioned clogging is substantially prevented. Wearing the artificial nose on a regular basis helps thereby, particularly with secretion, because, by moistening the mucous membranes in the trachea, secretion is reduced. Moisture and heat exchangers can also be equipped with a speech function, and are then referred to, as also set forth for the present invention, as speech valves, wherein, however, other terms, such as voice valve, are also popular.

DE 699 20 440 T2 discloses a generic device, referred to therein as a voice valve with a filter, wherein the voice valve serves as the connection to a tracheostoma, and has a regenerative filter for moisture and heat exchange during breathing through the voice valve, as well as a housing, which receives the filter, and a first opening on a filter side, for connecting to the tracheostoma, and at least one second opening on a side lying opposite the filter, connecting to the environment, and a manually operable valve element for blocking the passage of air through the filter, wherein a sleeve extends into the interior of the housing, and forms a valve seat, which defines the first opening, in order to engage with the valve element in a sealing manner, through a manual actuation thereof.

All of the devices disclosed in DE 699 20 440 T2 require that, with a closure of the proximal opening, the filter is at least partially compressed. Due to the elasticity of the filter material, the voice valve disclosed therein then transitions from the closure position to an open position. The disadvantage with this, in particular, is that on one hand, the filter material becomes fatigued through the compression and decompression during the transitions into the closure position and the open position of the voice valve, and on the other hand, the elastic property of the filter material weakens through use, such that a secure opening and closing is no longer obtained.

SUMMARY OF THE INVENTION

The present invention assumes the object of providing a generic speech valve, with which the disadvantages known from the prior art are avoided, and which, in particular, is designed to be durable, and requires the application of only a little force in the transitioning from an open position into a closure position, while still retaining functionality.

This object is achieved by a speech valve according to the invention, of the type specified in the introduction, wherein this furthermore comprises a piston-like valve element, wherein the filter is at least partially encompassed by the valve element, wherein the valve element can be moved onto a valve seat disposed on the proximal opening, in order to generate a closure position, and can be returned to the open position in a spring-loaded manner, and wherein the valve element has a lower end, facing the proximal opening, which is assigned to the valve seat, when it is in the open position, and forms a gap with the valve seat, in particular an annular gap, that is large enough to fulfill the breathing function, through which an airflow can be conducted. The housing of the speech valve according to the invention preferably comprises a cover part and a bottom part. It has at least one encompassing side wall. This can have openings. The at least one side wall at least partially encompasses the filter. The filter is at least partially received in the housing. The piston-like valve element is disposed at its upper surface in the vicinity of an undersurface of the cover part, or assigned to an opening in the upper surface of the cover part, and can also extend through this opening. It is substantially received in the housing. With the aforementioned embodiments, an actuation by the user by means of a finger is enabled, in that, either with an assignment to an opening, the piston-like valve element can be brought into contact with the proximal opening, and thus can also be moved toward the proximal opening, directly, by means of the finger, or, alternatively, the finger of the user only comes in indirect contact with the piston-like valve element, when, for example, at least a partial region of an upper surface of the cover part is made of an elastic plastic material, which is in contact with the upper surface of the valve element, or is disposed in the vicinity thereof, such that a movement of this elastic part of the upper surface of the cover part enables a movement of the valve element toward the proximal opening. It is particularly preferred that piston-like valve element has an operating element, which is also disposed on the valve element, facing the proximal opening, and a correct sensing, and thus also operating, of the valve element is enabled for the user. By way of example, the operating element can have a semi-circular cross section, having a circular design seen from above, and it is further preferred that, when, in particular, a central opening is provided in the cover part, it extends out of this, at least in part, in order to facilitate an operating of this speech valve according to the invention for the user.

The spring-loaded return guidance of the valve element into an open position of the speech valve advantageously occurs by means of at least one spring element. This can be designed as a compression spring and/or tension spring element. The at least one spring element can also be made, although this is not preferred, of an elastic material, e.g. a suitable plastic material, which is preferably designed in the manner of a foam. This is an alternative to a typical compression spring and/or tension element. The elastic material can likewise be designed as a filter material thereby. A double filtering can be obtained through the use, in particular, of a foam filter material, and the wearing comfort for the user can be improved as a result. The actual filter, which at least partially encompasses valve element, is preferably formed by a foamed material, in particular a plastic, but it can also be formed by nonwoven materials, paper, or suchlike. It can be designed as a fine and/or coarse filter, and in particular as a coarse filter, when, likewise, a filter-like material is used for the spring element, which is then preferably designed as a fine filter. A coarse filter has, in particular, larger pores/openings, in comparison with a fine filter, such that the passage of air occurs with less resistance than with a fine filter. The material for the filter and/or the spring element formed by a filter-like material, can be coated and/or impregnated thereby, with antistatic and/or antibacterial compositions, for example.

The valve element is preferably supported by means of a spring element in the housing. The at least one spring element can be designed in any manner. It can be designed, in particular, as an elastic, foam material, as described above, even if this is not preferred, but also, in particular, as a helical spring, a helical tension spring, conical spring, spiral spring, disk spring, annular spring, or pneumatic spring. Depending on the design of the at least one spring element, in particular as a compression spring element, corresponding bearings are to be provided, in which the spring elements are securely retained, or disposed. The spring-loaded bearing can be disposed thereby, preferably on a proximal first end of the speech valve according to the invention, at which the proximal opening is also disposed, or on a distal end, lying opposite this, i.e. the second end of the speech valve, lying away from the body, at which the cover part of the housing is also present. Advantageously, bearing means are provided on the piston-like valve element, which are assigned to counter-bearings in the region of the proximal first end and/or the distal second end of the speech valve according to the invention. The bearing means for the valve element can be realized thereby through recesses provided in its upper and/or lower surface, in which at least one spring element can engage, or through the provision of encompassing recesses or widenings, or edges, or widening elements applied thereto, or parts having a reduced diameter, such that bearing means are provided by the then resulting annular surfaces or annular surface sections, in which the at least one spring element can engage, or be suspended. The spring element(s) can also be attached at the proximal and/or distal ends thereof to the cover part or bottom part, e.g. through adhesive, in particular when this is designed as a tension spring element. In particular, an attachment to an undersurface of the cover part, or an upper surface of the bottom part, can be obtained, and a bearing can be provided on the opposite side of the spring element(s). The attachment can take place, for example, through the provision of suspension points for tension springs provided with end hooks, which are disposed, for example, on a suspension bridge, on at least one, preferably both, ends of the tension spring element.

The bearing means formed on the piston-like valve element can comprise devices that serve for receiving, retaining or positioning the at least one spring element. Thus, by way of example, the bearing means can have recesses or cup-like means for receiving helical springs, disk springs or annular springs, which are preferably circular, and can thus be referred to as cup-like recesses. The bearing means can also have protruding, cylindrical tube wall sections, optionally also in combination with the recesses referred to above, in order to improve, or enable, a retention, or guidance of the at least one spring element. Eyelets or suchlike can also be provided there, e.g. in order to attach helical springs. A projection or recess encompassed by the bearing means is preferably of such dimensions thereby, that an inner contour thereof is adapted to an outer contour of the spring element inserted therein.

The counter-bearing is preferably created by the cover part or the bottom part of the housing for the speech valve according to the invention, depending on whether the counter-bearing is disposed on the proximal end or distal end of the speech valve according to the invention.

When it is disposed on the proximal end of the speech valve, then recesses can be provided, for example, in the bottom part, which are preferably circular, and thus to be referred to as cup-like recesses, for receiving the spring elements, e.g. helical springs, et cetera. Accordingly, cylindrical tube wall sections can be provided as projections on the piston-like valve elements facing an upper surface of the bottom part, as is already described above in reference to the bearing means, provided by the valve element itself. Combinations of recesses and projections are also possible. The counter-bearing is preferably disposed in the vicinity of the proximal opening thereby, but can also be disposed on the bottom part at a spacing to an edge of an opening. There is always an assignment of the bearing means to the counter-bearing, in that, by way of example, when numerous spring elements are provided, which are disposed evenly or unevenly about a circumference of the piston-like spring element, corresponding counter-bearings are provided in the bottom part, engaging therewith.

Accordingly, with the design of a counter-bearing on the distal end and thus in the cover part of the housing of the speech valve according to the invention, at least one recess in an upper surface, in particular round, and thus to be referred to cup-shaped, is provided, in which the at least one spring element engages, and is retained, supported and/or positioned by this means. Accordingly, cylindrical tube wall sections can be disposed on an undersurface of the cover part, facing toward the piston-like valve element, or even just partial wall sections, as can also be the case with the other designs of the counter-bearing and the bearing means in which spring elements can be received. When the counter-bearing is disposed in the region of the cover part, then this is also assigned to the bearing means provided by the vale element. This means that, by way of example, when numerous spring elements are provided, which engage with the valve element, and are supported there by the bearing means, corresponding counter-bearings are to be provided in the cover part.

As set forth in the present invention, it can also be provided, however, that, by way of example, just one single spring element is provided. An exemplary embodiment for this would be, in a design of the spring element as a helical spring or a spiral spring, for example, or with a foamed elastic material having an annular design, it is disposed at an outer circumference, defined by the side walls of the piston-like valve element, such that the valve element is at least partially encompassed by the spring element. The bearing means, provided by the piston-like valve element, are then formed as a widening or an edge disposed on the side walls or disposed in the region of the proximal end of the housing for the speech valve according to the invention, wherein, when disposed on the side walls, for example, simply a recess may be provided there, in which the end of a helical spring, for example, engages. The counter-bearing can be provided in an embodiment of this type by an undersurface of the cover part. It is also possible thereby, that the cover part has, in particular, a central opening, through which the valve element can be operated, wherein, preferably, the valve element has an operating element disposed on its distal end.

It is particularly preferred that the valve element has at least one bearing means disposed on a side wall and/or an undersurface and/or an upper surface thereof. It is particularly preferred that at least one spring element is received in at least one recess in the valve element. The at least one recess is preferably disposed on the undersurface and/or upper surface of the valve element. The counter-bearing for the at least one spring element is advantageously provided by an undersurface of the cover part and/or an upper surface of the bottom part.

In a particularly preferred embodiment, the valve element comprises a widening on its lower end, facing toward the proximal opening, which protrudes over a side wall of the valve element, and preferably forms at least one engagement means, which serves, in particular, for retaining at least one spring element, in particular at least one tension spring element.

In a particularly preferred embodiment of the present invention, the valve element is disposed at least partially in the spring element. With an embodiment of this type, it may also be the case that only one single spring element is provided.

Insofar as the speech valve has a distal opening, basically lying opposite a proximal opening, particularly preferably in the cover part, in particular in order to improve or facilitate an operation of the piston-like valve element by the user, the valve element lies advantageously in a sealing manner on the opening. This can be obtained, for example, in that a sealing ring is provided on the edge of the opening in the cover part of the housing, or is provided, instead, on the upper surface or the side wall of the valve element. Corresponding sealing elements may also be disposed on both on the valve element and on the cover part, which, in particular, can interact by fitting into one another, for example. It may also be provided that, for example, the valve element has a soft, elastic plastic material, created by means of a 2-component transfer molding in the region of the upper surface or the side wall, via which a seal is then provided, if applicable in combination with other corresponding sealing means, disposed in the region of the distal opening in the cover part, or vice versa.

Accordingly, the proximal end can be sealed with the transition of the valve element from an open position into a closure position. Here as well, sealing means can be provided, in particular, on the opening edge or in the region of the proximal opening, which interact with the valve element. Corresponding sealing means can also be provided on the valve element, i.e. in particular at its proximal end. Sealing elements can also be provided on both the sealing element, in particular at its proximal end, and in the region of the side walls, as well as in the region of the proximal opening, or indirectly thereon, wherein then, the respective sealing elements can also interact, e.g. through the formation of a form fit. The valve element can also have an elastic material on its proximal end, e.g. on the undersurface facing toward the proximal opening, or, however, also in the region of the side walls, which can be obtained, e.g. by means of a 2-component transfer molding, by means of which elastic material a seal can be obtained. The explanations provided above in reference to the sealing of the opening in the cover part, which preferably lies opposite the proximal opening, apply accordingly.

Preferably the cover part of the housing for the speech valve according to the invention has at least one retaining means for the valve element. The retaining means can be formed thereby, in particular, as an integral part of the cover part, and can be provided, for example, by the upper surface of the cover part itself. A corresponding embodiment has, for example, a preferably central opening in the upper surface of the cover part, through which the valve element extends somewhat, and, if applicable, only an operating element disposed on the distal end thereof, for facilitating the operation of the speech valve by a user. The undersurface of the edge region of the cover part surrounding this opening then serves as a retaining means. Other types of retaining means can also be provided, however, which are disposed, for example, on the undersurface of the cover part, facing toward the proximal opening of the speech valve, which limit the spring travel of the valve element during the transition from the closure position into the open position. The latter is also the fundamental function that the retaining means must fulfill as set forth in the present invention. By way of example, a circular sealing ring can serve as the retaining means disposed on the undersurface of the cover part, which interacts with an upper surface or side wall of the valve element, and limits the spring travel thereby.

It is particularly preferred that the housing has at least one opening that is oriented perpendicular and/or parallel to a central main axis thereof. Preferably, numerous openings are provided, which are furthermore preferably disposed evenly on the outer circumference of the housing, preferably on the outer circumference of the cover part. Alternatively or in addition thereto, openings can also be provided in the cover part, which are oriented parallel to the central main axis. This can be realized, when the cover part extends beyond the bottom part, such that openings can be provided in the region of the extension, in a plane parallel to the upper surface of the cover part, and offset to the proximal end of the speech valve according to the invention. These then face toward the skin of the wearer with their orifices. It may also be provided that there is only one opening, when this has a sieve-like design, for example. As set forth in the present invention, the sieve itself is then referred to as a single opening thereby, and the individual openings in the sieve itself are not taken into account.

The at least one opening oriented perpendicular and/or parallel to the central main axis can take any form, and be designed, for example, as round, triangular or quadrangular, in particular square or rectangular, but also annular. Any other opening shape, however, is also possible. By way of example, a side wall of the cover part, which is oriented parallel to the central main axis, can have a number of rectangular openings, which are formed simply by bridges disposed between the upper surface of the cover part and an undersurface thereof, or, respectively, an upper surface of the bottom part, and thus provide a connection between the cover part and the bottom part of the housing. Advantageously, numerous openings are provided, separated from one another by bridges and/or wall sections. Wall sections are the regions, for example, that are between two adjacent circular openings in the side walls of the cover part, or in the region of the wall of an extension of the cover part, when openings are to be provided in a plane parallel to the upper surface of the cover part, and offset to the proximal end.

A connection between the cover part and bottom part can also be provided by means of bridges, or a delimiting wall with openings, that engage with the cover part and bottom part, and that are/is disposed in the interior of the housing, in particular, in the vicinity of the outer wall of the filter. A delimiting wall or bridges can also function as a receiver for the filter and/or a guide for the valve element, wherein a connection between the cover part and the bottom part is not necessary. By way of example, the bridges, or the delimiting wall, respectively, can be disposed on the undersurface of the cover part, and extend toward the bottom part, but end prior to the upper surface thereof, and vice versa.

A speech valve is provided by the present invention, which enables a secure closing, without the moisture exchange function of the filter becoming impaired due to compression and decompression. The valve element can be securely guided thereby, and also provides feedback to him, by means of the contact of the valve element with the valve seat, with the transition into the closure position, in that speech is only enabled in the closure position.

BRIEF DESCRIPTION OF THE DRAWINGS

The invention shall be explained in greater detail based on the following drawings and in which.

DETAILED DESCRIPTION OF THE PREFERRED EMBODIMENTS

Figure 1:
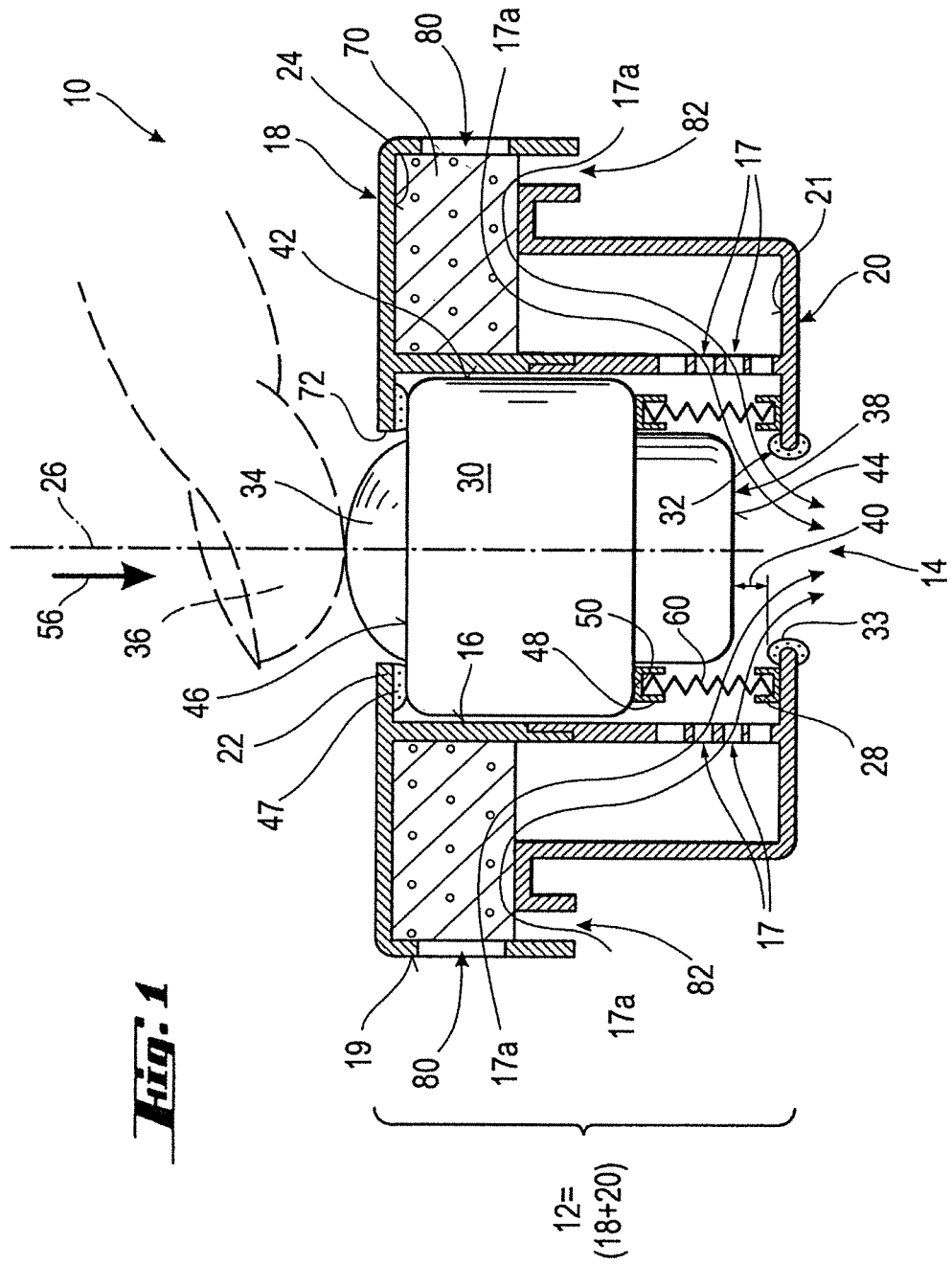
FIG. 1 shows a first embodiment of the speech valve according to the invention.
Figure 2:
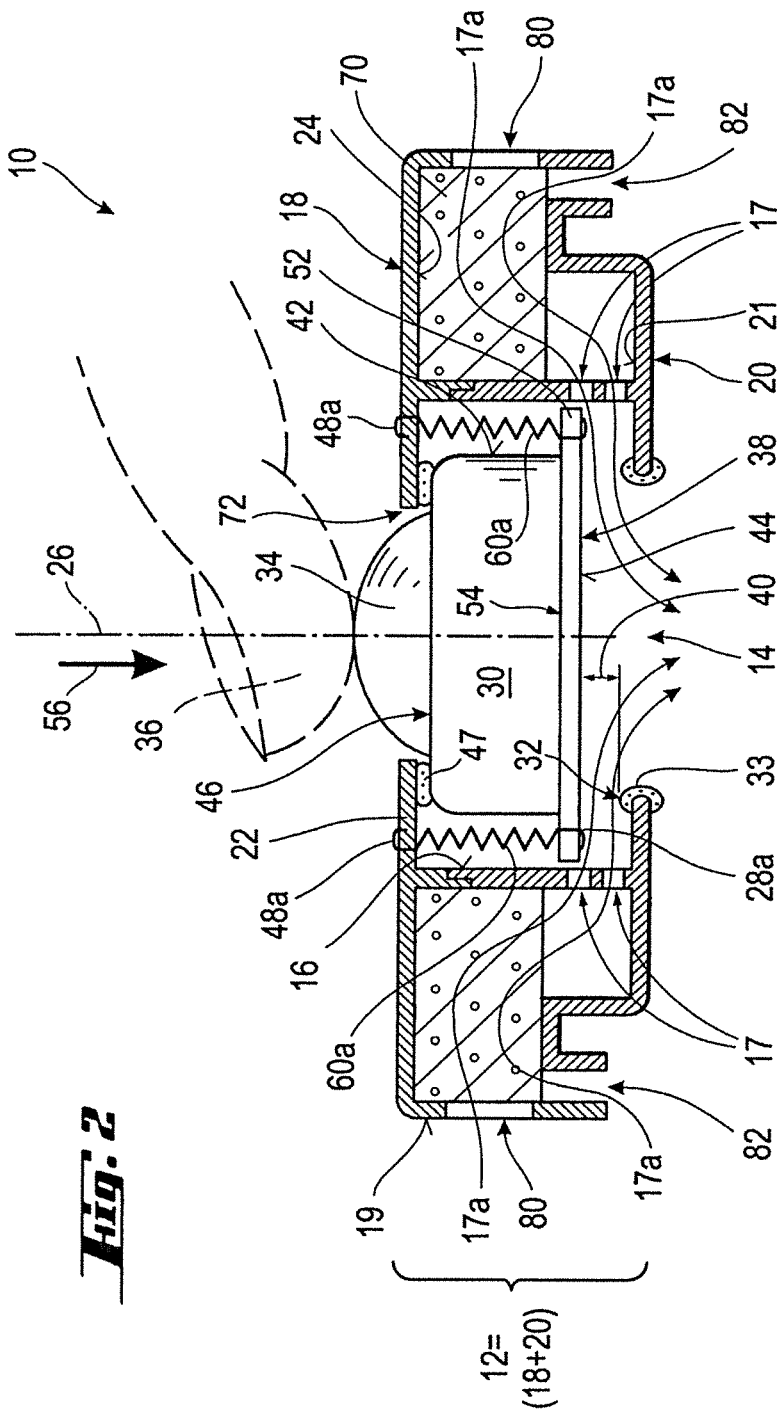
FIG. 2 shows a second embodiment of the speech valve according to the invention.
Figure 3:
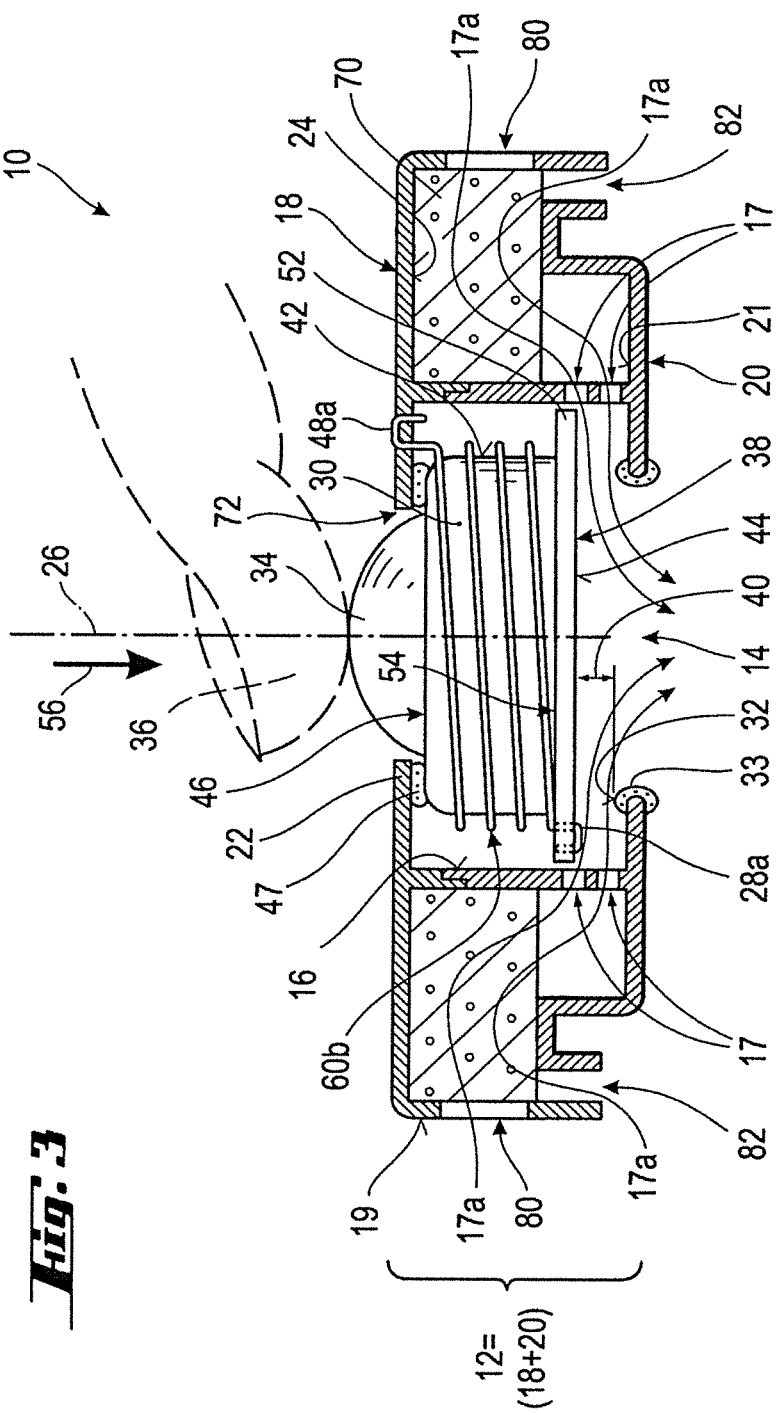
FIG. 3 shows a third embodiment of the speech valve according to the invention.

FIGS. 1 to 3 show the three embodiments of the speech valve according to the invention, in each case in a sectional view. It should first be noted that the invention is not limited to the combinations of features shown in the figures. Rather, the respective features disclosed in the description, including the description of the Figures, can be combined with those features indicated in the Figures. In particular, the design of the valve seat with a seal, shown in the Figures, is just one of the possible designs. A seal on the valve seat can also be omitted. Furthermore, any type of spring element, in particular including a plurality spring elements, can be provided and arranged in any manner, in order to enable a movability of a piston-like valve element. The at least one spring element can, by way of example, also be formed by an elastic plastic material, in particular foamed. Moreover, the filter material can not only be disposed directly adjacent to, thus bearing on, an undersurface of a cover part of the housing for the speech valve according to the invention, but rather, it can also extend to the upper surface of a bottom part of the housing, also bearing thereon, or, instead, it can assume any other extension between these two limits. Lastly, it should also be noted that the reference symbols recorded in the Claims should not in any way limit the scope of protection for the present invention, but rather, merely refer to the embodiments shown in the Figures. Moreover, in the three alternative embodiments, the same reference symbols are used for identical features, for purposes of simplification.

FIG. 1 shows, in an enlarged view, the first embodiment of the speech valve 10 according to the invention, having a housing 12, in the open position. The housing 12 has a proximal opening 14 in the vicinity of the body. The speech valve 10 is stuck onto a tracheal cannula or an adhesive bandage, not shown here, which is glued over the stoma of the wearer, by way of example. Typical connectors, in the DIN-norm as well, e.g. with a 15 mm or 20 mm diameter, are known for this.

The housing 12 has openings 80 oriented such that they are perpendicular in relation to a central main axis 26, and openings 82 that are oriented parallel thereto, through which air 17a can flow through a filter 70 in the interior of the housing 12 and into the stoma of a user via the proximal first opening 14, when the speech valve 10 is in the open position, and also flow out in the opposite direction via the proximal first opening 14, through the openings 80 and 82, after passing through the filter 70. The openings 80 and 82 (the latter can be left out, by way of example) have, for example, a sieve-like or circular design, and are disposed such that they are distributed evenly over the outer circumference of the cover part 18 in the side walls 19 and/or in a surface in the plane of the openings 82. A secure connection of the cover part 18 to the bottom part 20 is provided by means of bridges or other wall sections between the openings 80 and/or 82. The air flows thereby through a gap 40 disposed beneath one end of a delimiting wall 16, which is formed between a lower end 38 of a valve element 30, having a side wall 42, which is, designed in the manner of a piston, disposed in the housing 12, and a valve seat 32, having a seal 33, wherein the gap 40 is an annular gap. An airflow in the stoma of the patient, not shown here, through the proximal first opening 14, is prevented between a first lower end 38 of the valve element 30 and the valve seat 32, when in the closure position during a movement of the valve element 30 via an operating means 34 by means of a finger 36, indicated in a virtual manner, of a user, in the direction of the arrow 56, until the lower end 38 bears on the valve seat 32, and as a result, the user is able to speak, in particular as long as a voice prosthesis has been inserted therein after the larynx has been removed. The limiting wall 16 serves, for example, to provide a receiver for the filter 70, and also as an air guidance toward the gap 40. It is preferably designed as an encompassing cylindrical tube wall section on an undersurface 24 of a cover part 18, facing toward the proximal opening 14. The delimiting wall 16 can have openings 17 thereby, through which air flows 17a can flow toward the gap 40, or conversely, can be exhaled. As a result, a (further) connection between the cover part 18 and the bottom part 20 can be obtained, in order to stabilize the housing 12, by means of bridges or wall sections disposed between circular or sieve-like openings 17 in the delimiting wall 16. It is also possible, however, to provide no openings, and to end the delimiting wall 16, thereby, in particular at the height of a recess, in order to enable a passage of air toward the gap 40.

The piston-like valve element 30, designed with a cylindrical middle part, has the encompassing recess 50 at the lower end 38, by means of which, ultimately, a reduced diameter of the end 38 of the valve element 30 is provided for closing the valve seat 32, such that the proximal first opening 14 can also be smaller.

The annular surface formed by the recess 50 in the valve element 30 forms a bearing means 48 for spring elements 60, in this case compression spring elements 60. Even if the annular surface is adequate as a bearing means 48, cup-like receivers can supplement the bearing means 48 there, as shown, for example. The bearing means 48 could also be designed, for example, as recesses in the region of the recess 50 in the valve element 30. The first embodiment of the speech valve 10, shown in FIG. 1, has numerous spring elements 60 thereby, which are disposed such that they are distributed evenly about the lower end 38 of the valve element 30, having a reduced diameter as a result of the recess 50, and are supported on the annular surface formed by the recess 50. Alternatively, only a single spring element 60 may be provided, however, and in the case of numerous spring elements, four, six or eight, can be provided, for example, preferably evenly spaced to one another. As a single spring element, for example, one such as that made of a sufficiently elastic, foamed plastic material, as is also the case with the other embodiments according to FIGS. 2 and 3, can be used, which is designed as a fine filter, and has an annular shape.

An upper surface 21 of a bottom part 20 functions as the counter-bearing 28 for the spring elements 60, wherein retaining, or positioning, means can be provided on the upper surface 21 for retaining and/or positioning the spring element 60, or, respectively, in the form of cylindrical tube wall sections disposed on the upper surface 21 of the bottom part 20, the dimensions of which are adapted to an outer contour of the spring element 60. The lower end 38 of the tapered lower part of the valve element 30 has a flat design, having an undersurface 44 which extends over curves in the side walls of the valve element 30. The contact of the valve element 30 with the valve seat 32 is obtained in the region of these curves via an annular seal 33 of the valve seat 32, in order to prevent an air flow through the gap 40 of the speech valve 10 according to the invention.

In the open position shown in FIG. 1, the piston-like valve body 30 is pressed toward the undersurface 24 of the cover part 18 of the housing 12, due to the spring force of the spring element 60. The valve element 30 is held in position in the housing 12 by retaining means 22 provided on the cover part 18, which are preferably disposed encircling the operating element 34 of the valve element 30, but can otherwise be designed in the manner of bridges or other projections. Preferably, and as is shown in FIG. 1, a retaining means 22 is provided, which is integrated in the cover part 18 as an integral part thereof, such that the upper surface of the cover part 18 appears as a flat surface having a circular opening 72 when seen from above. The cover part 18 comprises the lateral wall 19, which is formed basically parallel to the main axis 26. Preferably, a sealing means 47 is disposed thereby on the upper surface 46 of the valve element 30, in particular, when the operating element 34 is provided, encircling this operating element, in order to provide a seal between the valve body 30 and the cover part 18, which has the retaining means 22. Alternatively, sealing materials can also be disposed on the undersurface 24 of the cover part 18 in the region of the retaining means 22. In a further preferred embodiment, sealing materials can be disposed on both the undersurface 24 of the cover part 18, in the region of the retaining means 22, as well as on the upper surface 46 of the valve element 30. The sealing material can be an integral part of the cover part 18 of the housing 12 and/or connected to the valve element 30. This can be obtained, for example, by means of a 2-component transfer molding in the production of the speech valve 10.

The filter 70 is neither compressed by the speech valve 10, nor otherwise moved. The filter 70 comprises the valve element. The filter 70 is assigned to the opening 70, and directly adjacent to the undersurface 20 of the cover part 18, as well as bearing thereon, if applicable, and attached thereto, if applicable, such that it is received in the housing 12. The filter 70 is disposed in the housing 12 such that it is spaced apart from the proximal first opening 14 and thus the upper surface 21 of the base 20.

The bearing means 48 and the counter-bearing 28, in each case a plurality thereof, can be designed in any manner. These can, for example, comprise cone-like projections, having a recess for receiving the spring element, or also be encircling walls or, however, an encircling annular surface, or, for example, cup-like recesses in the valve element 30, starting from a surface of the recess 50, reaching into the body of the valve element 30, in the case of the bearing means 48, wherein in the first case, an opposite wall is provided by the side walls 42 in the lower end 38 of the valve element 30, having a reduced diameter. A connection between the bottom part 20 and the cover part 18 can also be provided via bearing means 48 and counter bearing(s) 28.

After actuation in the direction of the arrow 56 by the user, the gap 40 between the lower end 38, or the undersurface 44 of the valve element 30 and the valve seat 32 is closed with the seal 33 disposed there, and as soon as the user no longer desires to speak, the valve element 30 is returned to the open position according to FIG. 1, by means of the spring element 60, by removing the pressure exerted on the spring element 60, i.e. by removing the finger 36 from the operating means 34, or reducing the pressure exerted on the spring element 60 by the finger.

FIG. 2 shows an alternative second embodiment of the speech valve 10 according to the invention, which, in differing from that in FIG. 1, is designed such that it is significantly shorter. The arrangement of the filter 70 corresponds to that in the first embodiment. Essentially, the valve element 30 has a different design, in that it has an additional widening 52 at its lower end 38, which extends beyond the side walls 42 of the valve element 30, and forms one or more engagement means 54, which is, or are, formed such that it, or they, encircle the side walls 52 of the valve element 30. The spring elements, in this case compression spring elements 60, preferably at least two, more preferably at least three, are permanently attached to the undersurface 24 of the cover part 18 at attachment points 48a. The widening 52 can provide, thereby, a closed, annular surface as the engagement means 54, but it can also have recesses, for example, such that the engagement means 54 are provided by means of the surfaces disposed between recesses, as long as a sealing of the valve seat 32 is ensured when the speech valve 10 according to the invention is in the closure position. Bearing means, in the form of circular recesses or protruding cylindrical tube wall sections, can also be provided on an upper surface of the widening 52 facing toward the cover part 18, for receiving spring elements 60. The engagement means 54 provide(s) attachment points 28a for numerous, preferably four, six or eight, tension spring elements 60a, preferably disposed evenly about the outer circumference of the valve element 30, designed, for example, as helical tension springs, having a reduced diameter, wherein attachment points are formed by the undersurface 24, with respect to the retaining means 22 of the cover part 18. The manner of functioning in the open and closure positions of the embodiment shown in FIG. 2 corresponds to that of the embodiment shown in FIG. 1.

FIG. 3 shows an alternative third embodiment of the speech valve 10 according to the invention. In differing from the embodiment shown in FIG. 2, only one helical spring 60b is provided, in which the valve element 30 is partially received, wherein the undersurface 24 of the cover part 18 serves as an attachment point 28b for the helical spring 60b. The other attachment point 28b for the helical spring 60b is formed by the widening 52 of the valve element 39, corresponding to the embodiment shown in FIG. 2.

The invention claimed is:

1. A speech valve for persons having undergone a laryngectomy or tracheotomy, comprising a housing with a proximal opening and a at least one filter at least partially received in the housing, the housing having a piston-like valve element, wherein the filter at least partially encompasses the valve element, wherein the housing includes a cover part having an opening for receiving the valve element, the proximal opening being located at an end of the housing opposite the cover part, wherein the valve element bears on the opening in a sealing manner, wherein the valve element is moved onto a valve seat disposed on the proximal opening in order to generate a closure position, and is returned to an open position of the speech valve in a spring-loaded manner, and wherein the valve element has a lower end facing toward the proximal opening, and when in the open position, forms a gap with the valve seat, through which an air flow is conducted.

2. The speech valve according to claim 1, wherein the valve element is supported in the housing via at least one spring element.

3. The speech valve according to claim 1, wherein the cover part has at least one retaining means for the valve element.

4. The speech valve according to claim 2, wherein the valve element has at least one bearing means for supporting the at least one spring element disposed on at least one of a side wall, an undersurface, and an upper surface thereof.

5. The speech valve according to claim 2, wherein the at least one spring element is received in at least one recess in the valve element.

6. The speech valve according to claim 2, comprising a counter-bearing for the at least one spring element which is provided by an undersurface of the cover part and/or an upper surface of a bottom part, which is comprised by the housing.

7. The speech valve according to claim 1, wherein the housing has at least one opening oriented at least one of perpendicular and parallel to a central main axis.

8. The speech valve according to claim 7, wherein the at least one opening is a plurality of openings separated from one another by at least one of bridges and wall sections.

9. The speech valve according to claim 2, wherein the valve element is disposed at least partially in the spring element.

* * * * *